(12) United States Patent
Fürsch et al.

(10) Patent No.: US 7,202,196 B2
(45) Date of Patent: Apr. 10, 2007

(54) SELECTIVE HERBICIDE COMPRISING A TETRAZOLINONE DERIVATIVE

(75) Inventors: Helmut Fürsch, Leichlingen (DE); Dieter Feucht, Monheim (DE); Thomas König, Hilden (DE); Hartwig Dauck, Bangkok (TH); Felicitos V. Palis, Laguna (PH); Ruperto P. Basilio, Laguna (PH)

(73) Assignee: Bayer Cropscience AG, Monheim (DE)

( * ) Notice: Subject to any disclaimer, the term of this patent is extended or adjusted under 35 U.S.C. 154(b) by 29 days.

(21) Appl. No.: 10/487,798

(22) PCT Filed: Aug. 19, 2002

(86) PCT No.: PCT/EP02/09238

§ 371 (c)(1),
(2), (4) Date: Nov. 24, 2004

(87) PCT Pub. No.: WO03/020035

PCT Pub. Date: Mar. 13, 2003

(65) Prior Publication Data

US 2005/0085388 A1    Apr. 21, 2005

(30) Foreign Application Priority Data

Aug. 30, 2001 (DE) ................................ 101 42 336

(51) Int. Cl.
```
A01N 25/32    (2006.01)
A01N 43/72    (2006.01)
A01N 43/64    (2006.01)
A01N 43/60    (2006.01)
A01N 43/58    (2006.01)
A01N 43/00    (2006.01)
```

(52) U.S. Cl. .............. 504/103; 504/132; 504/134; 504/136; 504/137; 504/139

(58) Field of Classification Search .............. 504/103, 504/132, 134, 136, 137, 139
See application file for complete search history.

(56) References Cited

U.S. PATENT DOCUMENTS

| | | | |
|---|---|---|---|
| 4,906,285 A | 3/1990 | Wada et al. ................... 71/92 |
| 5,081,244 A | 1/1992 | Wada et al. ................ 544/296 |
| 5,190,573 A | 3/1993 | Misslitz et al. ............. 504/292 |
| 5,281,571 A | 1/1994 | Woodard et al. ........... 504/225 |
| 5,332,717 A | 7/1994 | Lüthy et al. ................ 504/242 |
| 5,362,704 A * | 11/1994 | Goto et al. ................. 504/134 |
| 5,428,002 A | 6/1995 | Lüthy et al. ................ 504/230 |
| 5,489,571 A | 2/1996 | Woodard et al. ........... 504/280 |
| 5,494,886 A | 2/1996 | Kehne et al. ............... 504/215 |
| 5,496,956 A | 3/1996 | Woodard et al. ........ 548/377.1 |
| 5,521,146 A | 5/1996 | Hur et al. ................... 504/243 |
| 5,529,976 A | 6/1996 | Kehne et al. ............... 504/213 |
| 5,530,126 A | 6/1996 | Woodard et al. ............. 544/52 |
| 5,536,700 A | 7/1996 | Woodard et al. ........... 504/128 |
| 5,576,440 A | 11/1996 | Kehne et al. ............... 546/294 |
| 5,580,986 A | 12/1996 | Dorfmeister et al. ..... 548/371.7 |
| 5,600,008 A | 2/1997 | Hamper et al. ............. 568/314 |
| 5,600,016 A | 2/1997 | Hamper et al. ............. 568/437 |
| 5,635,451 A | 6/1997 | Kehne et al. ............... 504/215 |
| 5,756,424 A | 5/1998 | Dorfmeister et al. ....... 504/246 |
| 5,759,958 A | 6/1998 | Endo et al. ................. 504/273 |
| 5,846,907 A | 12/1998 | von Deyn et al. .......... 504/221 |
| 5,866,723 A | 2/1999 | Hamper et al. ............. 568/335 |
| 5,869,686 A | 2/1999 | Dorfmeister et al. ..... 548/365.4 |
| 5,928,991 A | 7/1999 | Fürsch et al. ............... 504/103 |
| 6,077,813 A | 6/2000 | Linker et al. ............... 504/272 |
| 6,077,814 A | 6/2000 | Morita et al. ............... 504/273 |
| 6,124,469 A | 9/2000 | Rheinheimer et al. ...... 548/240 |
| 6,165,944 A | 12/2000 | von Deyn et al. .......... 504/271 |
| 6,235,680 B1 | 5/2001 | Ziemer et al. .............. 504/112 |
| 6,251,827 B1 | 6/2001 | Ziemer et al. .............. 504/130 |
| 6,331,507 B1 | 12/2001 | Linker et al. ............... 504/244 |
| 6,420,316 B1 | 7/2002 | Linker et al. ............... 504/273 |
| 6,451,736 B1 | 9/2002 | Linker et al. ............... 504/210 |
| 6,492,301 B1 | 12/2002 | Hacker et al. .............. 504/128 |
| 2002/0025910 A1 | 2/2002 | Deyn et al. ................. 504/263 |
| 2002/0123428 A1 | 9/2002 | Hacker et al. .............. 504/139 |
| 2003/0069138 A1 | 4/2003 | Hacker et al. .............. 504/144 |
| 2003/0191025 A1 | 10/2003 | Hacker et al. .............. 504/133 |

FOREIGN PATENT DOCUMENTS

| | | |
|---|---|---|
| CA | 2388745 | 4/2001 |
| DE | 199 47 918 | 4/2001 |
| EP | 612 735 | 8/1994 |
| JP | 9-12406 | 1/1997 |

(Continued)

OTHER PUBLICATIONS

**Patent Abstracts of Japan, vol. 015, No. 306 (C-0856), Aug. 6, 1991 & JP 03 115205 A (Kumiai Chem Ind Co Ltd), May 16, 1991 abstract.

(Continued)

Primary Examiner—Shelley A. Dodson
(74) Attorney, Agent, or Firm—Richard E. L. Henderson

(57) ABSTRACT

The invention relates to novel herbicidal synergistic active compound combinations comprising a known tetrazolinone derivative and known herbicidally active compounds and/or safeners, which compositions can be used with particularly good results for the selective control of weeds in various crops of useful plants.

9 Claims, No Drawings

FOREIGN PATENT DOCUMENTS

| | | |
|---|---|---|
| JP | 10-330202 | 12/1998 |
| JP | 11-335212 | 12/1999 |
| JP | 2000-239111 | 9/2000 |
| WO | 99/03348 | 1/1999 |

OTHER PUBLICATIONS

**Patent Abstracts of Japan, vol. 1998 No. 1, Jan. 30, 1998 & JP 09 241109 A (Nippon Bayeragrochem KK), Sep. 16, 1997 abstract.

* cited by examiner

SELECTIVE HERBICIDE COMPRISING A TETRAZOLINONE DERIVATIVE

The present patent application has been filed under 35 U.S.C. 371 as a national stage application of PCT/EP02/09238, filed Aug. 19, 2002, which was published in German as International Patent Publication WO 03/020035 on Mar. 13, 2003, which is entitled to the right of priority of German Patent Application 101 42 336.5, filed Aug. 30, 2001.

The invention relates to novel herbicidal synergistic active compound combinations comprising a known tetrazolinone derivative and known herbicidally active compounds and/or safeners, which compositions can be used with particularly good results for the selective control of weeds in various crops of useful plants.

The tetrazolinone derivative 4-(2-chlorophenyl)-N-cyclohexyl-N-ethyl-4,5-dihydro-5-oxo-1H-tetrazole-1-carboxamide (common name: fentrazamide) is, as a broadly active herbicide, alone or in mixtures with other herbicides, the subject of a number of patent applications (cf U.S. Pat. No. 5,362,704; JP 11335212 A; JP 2000239111 A; JP 10330202; JP 09241109 A; JP 09012406 A; U.S. Pat. No. 5,928,991; WO 00/003591; WO 00/003597). However, the known herbicidal combinations have a number of gaps in their activity, and their compatibility with crop plants is likewise not under all conditions entirely satisfactory.

Surprisingly, it has now been found that the compound 4-(2-chlorophenyl)-N-cyclo-hexyl-N-ethyl-4,5-dihydro-5-oxo-1H-tetrazole-1-carboxamide, when used together with known herbicidally active compounds from various classes of substances, shows pronounced synergistic effects with respect to the activity against weeds and can be used particularly advantageously as broadly active combination preparations for the selective control of weeds in crops of useful plants such as, for example, rice.

Surprisingly, it has also been found that the compound 4-(2-chlorophenyl)-N-cyclo-hexyl-N-ethyl-4,5-dihydro-5-oxo-1H-tetrazole-1-carboxamide, alone or together with known herbicidally active compounds, can, when used together with the crop-plant-compatibility-improving compounds (safeners/antidotes) described below, prevent damage to the crop plants extremely efficiently and can therefore be used in a particularly advantageous manner as a broadly active combination preparation for the selective control of weeds in crops of useful plants such as cereals, for example wheat, barley, rye and rice.

The present invention provides selective herbicidal compositions, comprising an effective amount of an active compound combination comprising (a) the compound 4-(2-chlorophenyl)-N-cyclohexyl-N-ethyl-4,5-dihydro-5-oxo-1H-tetrazole-1-carboxamide (fentrazamide) of the general formula (I)

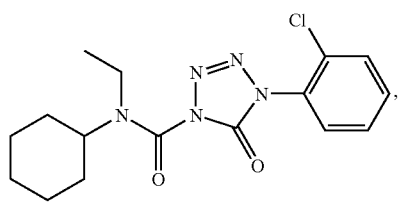

("active compound 1")

and (b) one or more compounds from a second group of herbicides comprising the active compounds listed below: 2,6-bis[[(4,6-dimethoxy-2-pyrimidinyl)oxy]benzoic acid and its salts, for example the sodium salt (bispyribac-sodium, known from EP-A 321 846), diphenylmethanone O-[2,6-bis[(4,6-dimethoxy-2-pyrimidinyl)oxy]benzoyl]-oxime (pyribenzoxim, known from EP-A 658 549), 7-[(4,6-dimethoxy-2-pyrimidinyl)thio]-3-methyl-1 (3H)-isobenzofuranone (pyriftalid, known from WO 91/05781), 1-(3-chloro-4,5,6,7-tetrahydropyrazolo[1,5-a]pyridin-2-yl)-5-(methyl-2-propynylamino)-1H-pyrazole-4-carbonitrile (pyraclonil, known from WO 94/08999), N-(2,6-dichloro-3-methylphenyl)-5,7-dimethoxy-[1,2,4]-triazolo[1,5-a]pyrimidine-2-sulphonamide (metosulam), 2-[[[[(4-methoxy-6-methyl-1,3,5-triazin-2-yl)amino]carbonyl]amino]sulphonyl]-benzoic acid (metsulfuron), methyl 3-chloro-5-[[[[(4,6-dimethoxy-2-pyrimidinyl)amino]carbonyl]amino]sulphonyl]-1-methyl-1H-pyrazole-4-carboxylate (halosulfuron), α-2-dichloro-5-[4-(difluoromethyl)-4,5-dihydro-3-methyl-5-oxo-1H-1,2,4-triazol-1-yl]-4-fluorobenzenepropanoic acid esters, in particular the ethyl ester (carfentrazone-ethyl), 4-[2-chloro-3-(4,5-dihydroisoxazol-3-yl)-4-methylsulphonyl-benzoyl]-5-hydroxy-1-methyl-1H-pyrazole (known from WO 98/31681), 1-methylethyl 5-[4-bromo-1-methyl-5-(trifluoromethyl)-1H-pyrazol-3-yl]-2-chloro-4-fluorobenzoate (fluazolate, known from WO 92/06962), 2-[1-[[2-(4-chlorophenoxy)propoxy]amino]-butyl]-5-(tetrahydro-2H-thiopyran-3-yl)-1,3-cyclohexanedione (clefoxydim, known from EP 456112), N-(2,4-difluorophenyl-1,5-dihydro-N-i-propyl-5-oxo-1-[(tetrahydro-2H-pyran-2-yl)methyl]-4H-1,2,4-triazole-4-carboxamide (HOK-201—cf. WO-A-98/38176/U.S. Pat. No. 6,077, 814), 4-(7-chloro-2,4-dimethyl-5-benzofuranyl)-2,4-dihydro-2-methyl-5-trifluoromethyl-3H-1,2,4-triazol-3-thione (OK-701—cf. WO-A-97/09326/U.S. Pat. No. 5,759,958), [2-chloro-3-(4,5-dihydro-3-isoxazolyl)-4-methylsulphonylphenyl]-(5-hydroxy-1-methyl-1H-pyrazol-4-yl)methanone (cf. WO-A-96/26206, WO-A-98/31681), [3-(4,5-dihydro-3-isoxazolyl)-2-methyl-4-methylsulphonylphenyl]-(5-hydroxy-1-methyl-1H-pyrazol-4-yl)methanone (cf. WO-A-96/26206, WO-A-98/31681), [3-[2-chloro-3-[(2,6-dioxocyclohexyl)carbonyl]-6-ethylsulphonylphenyl]-5-isoxazolyl]acetonitrile (cf. WO-A-01/28341), 2-[2-chloro-4-methylsulphonyl-3-[(2,2,2-trifluoroethoxy)methyl]benzoyl]-1,3-cyclohexanedione (cf. WO-A-01/28341) and 2-[[5,8-dimethyl-1,1-dioxido-4-(2-pyrimidinyl-oxy)-3,4-dihydro-2H-thiochromen-6-yl]-carbonyl]-1,3-cyclohexanedione (cf. WO-A-01/28341);

("active compound of group 2"), and, if appropriate, (c) at least one compound which improves crop plant compatibility, from the following group of compounds: α-(1,3-dioxolan-2-ylmethoximino)phenylacetonitrile (oxabetrinil), α-(cyano-methoximino)phenylacetonitrile (cyometrinil), 4-chloro-N-(1,3-dioxolan-2-ylmethoxy)-α-trifluoroacetophenone oxime (fluxofenim), 4,6-dichloro-2-phenylpyrimidine (fenclorim), 4-dichloroacetyl-3,4-dihydro-3-methyl-2H-1,4-benzoxazine (benoxacor), 1-methylhexyl 5-chloroquinoxaline-8-oxyacetate (cloquintocet), 2,2-dichloro-N-(2-oxo-2-(2-propenylamino)ethyl)-N-(2-propenyl)acetamide (DKA-24), 1,8-naphthalic anhydride, ethyl 1-(2,4-di-chlorophenyl)-5-trichloromethyl-1H-1,2,4-triazole-3-carboxylate (fenchlorazole ethyl), phenylmethyl 2-chloro-4-trifluoromethylthiazole-5-carboxylate (flurazole), 3-dichloroacetyl-5-(2-furanyl)-2,2-dimethyloxazolidine (furilazole, MON-13900), 4-dichloroacetyl-1-oxa-4-azaspiro[4.5]decane (AD-67), 2-dichloromethyl-2-methyl-1,3-dioxolane (MG-191), 2,2-dichloro-N-(1,3-dioxolan-2-ylmethyl)-N-(2-propenyl)acetamide (PPG-1292), 2,2-dichloro-N,N-di-2-propenylacetamide (dichlormid), N-(4-methylphenyl)-N'-(1-methyl-1-phenylethyl)urea (dymron), 1-dichloroacetylhexahydro-3,3,8a-trimethyl-pyrrolo[1,2-a]pyrimidin-6(2H)one (BAS-145138), N-(2-methoxybenzoyl)-4-(methylaminocarbonylamino)benzenesulphonamide, ethyl 4,5-dihydro-5,5-diphenyl-3-isoxazolecarboxylate (isoxadifen-ethyl), (4-chloro-2-methylphenoxy)acetic acid (MCPA), 2-(4-chloro-2-methylphenoxy)propionic acid (meco-prop), diethyl-1-(2,4-dichlorophenyl)-4,5-dihydro-5-methyl-1H-pyrazol-3,5-dicarboxylate (mefenpyr-diethyl) and 2,4-dichlorophenoxyacetic acid (2,4-D) and its derivatives, 4-(2-chlorobenzoylaminosulphonyl)-N-propylbenzamide and other N-(phenylsulphamoyl)benzanmide derivatives of the formula (II)

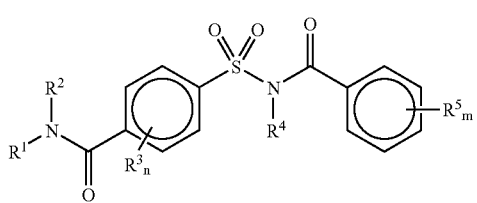

(II)

in which
$R^1$ represents hydrogen, $(C_1–C_6)$-alkyl, $(C_3–C_6)$-cycloalkyl, $(C_2–C_6)$-alkenyl, $(C_5–C_6)$-cycloalkenyl, phenyl or 3- to 6-membered heterocyclyl having up to 3 hetero atoms from the group consisting of nitrogen, oxygen and sulphur, where the six last-mentioned radicals are optionally substituted by one or more identical or different substituents from the group consisting of halogen, $(C_1–C_6)$-alkoxy, $(C_1–C_6)$-haloalkoxy, $(C_1–C_2)$-alkylsulphinyl, $(C_1–C_2)$-alkylsulphonyl, $(C_3–C_6)$-cycloalkyl, $(C_1–C_4)$-alkoxycarbonyl, $(C_1–C_4)$-alkylcarbonyl and phenyl and, in the case of cyclic radicals, also $(C_1–C_4)$-alkyl and $(C_1–C_4)$-haloalkyl;
$R^2$ represents hydrogen, $(C_1–C_6)$-alkyl, $(C_2–C_6)$-alkenyl, $(C_2–C_6)$-alkynyl, where the three last-mentioned radicals are optionally substituted by one or more identical or different substituents from the group consisting of halogen, hydroxyl, $(C_1–C_4)$-alkyl, $(C_1–C_4)$-alkoxy and $(C_1–C_4)$-alkylthio;
$R^3$ represents halogen, $(C_1–C_4)$-haloalkyl, $(C_1–C_4)$-haloalkoxy, nitro, $(C_1–C_4)$-alkyl, $(C_1–C_4)$-alkoxy, $(C_1–C_4)$-alkylsulphonyl, $(C_1–C_4)$-alkoxycarbonyl or $(C_1–C_4)$-alkylcarbonyl;
$R^4$ represents hydrogen or methyl;
$R^5$ represents halogen, nitro, $(C_1–C_4)$-alkyl, $(C_1–C_4)$-haloalkyl, $(C_1–C_4)$-haloalkoxy, $(C_3–C_6)$-cycloalkyl, phenyl, $(C_1–C_4)$-alkoxy, cyano, $(C_1–C_4)$-alkylthio, $(C_1–C_4)$-alkylsulphinyl, $(C_1–C_4)$-alkylsulphonyl, $(C_1–C_4)$-alkoxycarbonyl or $(C_1–C_4)$-alkylcarbonyl;
n represents 0, 1 or 2 and
m represents 1 or 2,
and their salts, in particular the sodium salts (known from WO-099/16744) or 2-methoxy-N-[4-(2-methoxybenzoyl-sulphamoyl)phenyl]acetamide and other N-acylsulphonamide derivatives of the formula (III)

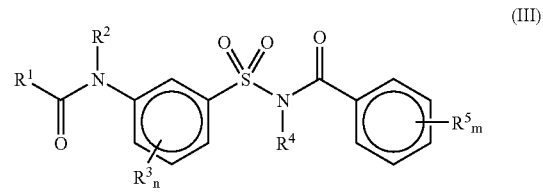

(III)

in which
$R^1$ represents hydrogen, $(C_1–C_6)$-alkyl, $(C_3–C_6)$-cycloalkyl, furanyl or thienyl, where each of the four last-mentioned radicals is unsubstituted or substituted by one or more substituents from the group consisting of halogen, $(C_1–C_4)$-alkoxy, halo-$(C_1–C_6)$-alkoxy and $(C_1–C_4)$-alkylthio and, in the case of cyclic radicals, also $(C_1–C_4)$-alkyl and $(C_1–C_4)$-haloalkyl;
$R^2$ represents hydrogen or methyl;
$R^3$ represents halogen, halo-$(C_1–C_4)$-alkyl, halo-$(C_1–C_4)$-alkoxy, $(C_1–C_4)$-alkyl, $(C_1–C_4)$-alkoxy, $(C_1–C_4)$-alkylsulphonyl, $(C_1–C_4)$-alkoxy-carbonyl or $(C_1–C_4)$-alkylcarbonyl;
$R^4$ represents hydrogen or methyl;
$R^5$ represents halogen, $(C_1–C_4)$-alkyl, halo-$(C_1–C_4)$-alkyl, halo-$(C_1–C_4)$-alkoxy, $(C_3–C_6)$-cycloalkyl, phenyl, $(C_1–C_4)$-alkoxy, cyano, $(C_1–C_4)$-alkylthio, $(C_1–C_4)$-alkylsulphinyl, $(C_1–C_4)$-alkylsulphonyl, $(C_1–C_4)$-alkoxycarbonyl or $(C_1–C_4)$-alkylcarbonyl;
n represents 0, 1 or 2 and
m represents 1 or 2,
and their alkali metal salts, in particular the sodium salts (known from DE-A1-19 621 522)
("active compounds of group 3").

As components for mixtures preference is given to the following active compounds of group 2:
bispyribac-sodium and pyribenzoxim.

Surprisingly, it has now been found that the active compound combinations defined above of the tetrazolinone derivative of the formula (I) and the active compounds of group 2 listed above in combination with active compounds of group 3, whilst being very well tolerated by useful plants, have particularly high herbicidal activity and can be used in a variety of crops, in particular in rice, but also in maize and cereals, for the selective control of weeds.

Surprisingly, the herbicidal activity of the active compound combinations according to the invention of compounds of the abovementioned groups 1 and 2 is considerably higher than the sum of the activities of the individual active compounds.

This means that there is not only a complementary action but also an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides of the prior art.

Moreover, surprisingly, it has been found that the active compound combinations defined above of the tetrazolinone derivative of the formula (I) and a safener/antidote ("active compounds of group 3") in combination with one or more of the active compounds of group 2 listed above, in addition to being very well tolerated by useful plants, have particularly high herbicidal activity and can be used in a variety of crops, in particular in cereal, especially wheat, but also in soybeans, potatoes, maize and rice, for the selective control of weeds.

It is furthermore surprising that, from a large number of known safeners or antidotes capable of antagonizing the damaging effect of a herbicide on the crop plants, it is specifically the compounds of group (c) listed above which neutralize the damaging effect of compounds of the formula (I) and their salts, if appropriate in combination with one or more of the active compounds of group 2 listed above, on the crop plants virtually completely without adversely affecting the herbicidal activity against the weeds.

It may be mentioned that the compositions according to the invention can be modified such that, in addition to components (a) and (b), they comprise, as third or further herbicidally active compound, one or more of the following active compounds:

2-chloro-N-(ethoxymethyl)-N-(2-ethyl-6-methylphenyl)acetamide (acetochlor), 5-(2-chloro-4-trifluoromethylphenoxy)-2-nitrobenzoic acid sodium salt (acifluorfen-sodium), 2-chloro-6-nitro-3-phenoxybenzeneamine (aclonifen), 2-chloro-N-(methoxymethyl)-N-(2,6-diethylphenyl)acetamide (alachlor), N-ethyl-N'-i-propyl-6-methylthio-1,3,5-triazine-2,4-diamine (ametryn), 4-amino-N-(1,1-dimethylethyl)-4,5-dihydro-3-(1-methylethyl)-5-oxo-1H-1,2,4-triazole-1-carboxamide (amicarbazone), N-(4,6-dimethoxy-pyrimidin-2-yl)-N'-(N-methyl-N-methylsulphonylsulphamoyl)-urea (amidosulfuron), 1H-1,2,4-triazol-3-amine (amitrole), S-[2-[(4-chlorophenyl)-(1-isopropyl)amino]-2-oxoethyl]O,O-dimethyl phosphorodithioate (anilofos), 6-chloro-4-ethylamino-2-isopropylamino-1,3,5-triazine (atrazine), 2-[2,4-dichloro-5-(2-propynyloxy)phenyl]-5,6,7,8-tetrahydro-1,2,4-triazolo-[4,3-a]-pyridin-3(2H)-one (azafenidin), N-(4,6-dimethoxypyrimidin-2-yl)-N'-[1-methyl-4-(2-methyl-2H-tetrazol-5-yl)-1H-pyrazol-5-ylsulphonyl]urea (azimsulfuron), N-benzyl-2-(4-fluoro-3-trifluoromethylphenoxy)butanamide (beflubutamid), 4-chloro-2-oxo-3 (2H)-benzothiazoleacetic acid (benazolin), N-butyl-N-ethyl-2,6-dinitro-4-trifluoromethyl-benzene-amine (benfluralin), 2,3-dihydro-3,3-dimethyl-5-benzofuranylethanesulphonate (benfuresate), N-(4,6-dimethoxypyrimidin-2-yl)-N'-(2-methoxycarbonylphenylmethyl-sulphonyl)urea (bensulfuron-methyl), S-[(4-chlorophenyl) methyl]diethylthiocarbamate (benthiocarb, thiobencarb), methyl 2-[2-[4-(3,6-dihydro-3-methyl-2,6-dioxo-4-trifluoromethyl-1(2H)-pyrimidinylphenoxymethyl]-5-ethylphenoxypropanoate (benzfendizone), 3-(2-chloro-4-methylsulphonylbenzoyl)-4-phenylthio-bicyclo-[3.2.1]-oct-3-en-2-one (benzobicyclon), 2-[[4-(2,4-dichloro-3-methyl-benzoyl)-1,3-dimethyl-1H-pyrazol-5-yl]-oxy]-1-(4-methylphenyl)ethanone (benzofenap), ethyl N-benzoyl-N-(3,4-dichlorophenyl)-DL-alaninate (benzoylprop-ethyl), 3-i-propyl-1H-2,1,3-benzothiadiazin-4 (3H)-one (bentazone), methyl 5-(2,4-dichlorophenoxy)-2-nitrobenzoate (bifenox), 5-bromo-6-methyl-3-(1-methylpropyl)-2,4(1H,3H)pyrimidinedione (bromacil), 2-bromo-3,3-dimethyl-N-(1-methyl-1-phenylethyl)butanamide (bromobutide), 3,5-dibromo-4-hydroxy-benzaldehyde O-(2,4-dinitrophenyl)-oxime (bromofenoxim), 3,5-dibromo-4-hydroxybenzonitrile (bromoxynil), N-butoxymethyl-2-chloro-N-(2,6-diethylphenyl)acetamide (butachlor), [1,1-dimethyl-2-oxo-2-(2-propenyloxy)] ethyl 2-chloro-5-(3,6-dihydro-3-methyl-2,6-dioxo-4-trifluoromethyl-1(2H)-pyrimidinyl)benzoate (butafenacil-allyl), 2-(1-ethoximinopropyl)-3-hydroxy-5-[2,4,6-trimethyl-3-(1-oxobutyl)phenyl]-2-cyclohexen-1-one (butroxydim), S-ethyl bis-(2-methylpropyl)thiocarbamate (butylate), N,N-diethyl-3-(2,4,6-trimethylphenylsulphonyl)-1H-1,2,4-triazole-1-carboxamide (cafenstrole), 2-[1-[(3-chloro-2-propenyl)oxyimino]propyl]-3-hydroxy-5-(tetrahydro-2H-pyran-4-yl)-2-cyclohexen-1-one (caloxydim, tepraloxydim), 2-(4-chloro-2-fluoro-5-(2-chloro-2-ethoxycarbonylethyl)phenyl)-4-difluoromethyl-5-methyl-2,4-dihydro-3H-1,2,4-triazol-3-one (carfentrazone-ethyl), 2,4-dichloro-1-(3-methoxy-4-nitrophenoxy)-benzene (chlomethoxyfen), 3-amino-2,5-dichlorobenzoic acid (chloramben), N-(4-chloro-6-methoxypyrimidin-2-yl)-N'-(2-ethoxycarbonylphenylsulphonyl)-urea (chlorimuron-ethyl), 1,3,5-trichloro-2-(4-nitrophenoxy)benzene (chlornitrofen), N-(4-methoxy-6-methyl-1,3,5-triazin-2-yl)-N'-(2-chlorophenylsulphonyl)urea (chlorsulfuron), N'-(3-chloro-4-methylphenyl)-N,N-dimethylurea (chlortoluron), ethyl 2-chloro-3-[2-chloro-5-(1,3,4,5,6,7-hexahydro-1,3-dioxo-2H-isoindol-2-yl)-phenyl]-2-propanoate (cinidon-ethyl), exo-1-methyl-4-isopropyl-2-(2-methylphenylmethoxy)-7-oxabicyclo-[2.2.1]-heptane (cinmethylin), N-(4,6-dimethoxy-1,3,5-triazin-2-yl)-N'-(2-(2-methoxyethoxy)phenylsulphonyl)urea (cinosulfuron), 2-[1-[2-(4-chloro-phenoxy)propoxyaminobutyl]-5-(tetrahydro-2H-thiopyran-3-yl)-1,3-cyclohexanedione (clefoxydim), (E,E)-(+)-2-[1-[[(3-chloro-2-propenyl)oxy] imino]propyl]-3-hydroxy-2-cyclohexen-1-one (clethodim), (R)-(2-propynyl) 2-[4-(5-chloro-3-fluoropyridin-2-yloxy)phenoxypropanoate (clodinafop-propargyl), 2-(2,4-dichloro-3-methylphenoxy)-N-phenylpropanamide (clomeprop), 3,6-dichloropyridine-2-carboxylic acid (clopyralid), methyl 3-chloro-2-[(5-ethoxy-7-fluoro[1,2,4]triazolo-[1,5-c]pyrimidin-2-ylsulphonyl)amino]benzoate (cloransulam-methyl), N-[(2-chlorophenyl)methyl]-N'-(1-methyl-1-phenylethyl) urea (cumyluron), 2-chloro-4-ethylamino-6-(1-cyano-1-methylethylamino)-1,3,5-triazine (cyanazine), N-(4,6-dimethoxypyrimidin-2-yl)-N'-(2-cyclopropylcarbonylphenylsulphonyl)urea (cyclosulfamuron), 2-(1-ethoximinobutyl)-3-hydroxy-5-(tetrahydro-2H-thiopyran-3-yl)-2-cyclohexen-1-one (cycloxydim), (R)-2-butyl [4-(4-cyano-2-fluorophenoxy) phenoxy]-propanoate (cyhalofop-butyl), 2,4-dichlorophenoxyacetic acid (2,4-D), 3,6-dichloro-2-methoxybenzoic acid (dicamba), (R)-2-(2,4-dichlorophenoxy)propanoic acid (dichlorprop-P), methyl 2-[4-(2,4-dichlorophenoxy)phenoxy]propanoate (diclofop-methyl), N-(2,6-dichlorophenyl)-5-ethoxy-7-fluoro-[1,2,4]-triazolo-[1,5-c]-pyrimidine-2-sulphonamide (diclosulam), 1,2-dimethyl-3,5-diphenyl-1H-pyrazolium methylsulphate (difenzoquat), N-(2,4-difluorophenyl)-2-(3-trifluoromethylphenoxy)pyridine-3-carboxamide (diflufenican), 2-[1-[(3,5-difluorophenyl)-aminocarbonylhydrazono]ethyl]pyridine-3-carboxylic acid (diflufenzopyr), S-(1-methyl-1-phenylethyl)-1-piperidine carbothioate (dimepiperate), 2-chloro-N-(2,6-dimethylphenyl)-N-(2-methoxyethyl)acetamide (dimethachlor), N-(1,2-dimethylpropyl)-N'-ethyl-6-methylthio-1,3,5-triazine-2,4-diamine (dimethametryn), (S-) 2-chloro-N-(2,4-dimethyl-3-thienyl)-N-(2-methoxy-1-methylethyl)acetamide ((S-) (dimethenamid)), 2-amino-4-(1-fluoro-1-methylethyl)-6-(1-methyl-2-(3,5-dimethylphenoxy)ethylamino)-1,3,5-triazine (dimexyflam), N3,N3-diethyl-2,4-dinitro-6-trifluoromethyl-1,3-diaminobenzene (dinitramine), 6,7-dihydrodipyrido[1,2-a:2',1'-c]pyrazinediium (diquat), S,S-dimethyl 2-difluoromethyl-4-i-butyl- 6-trifluoromethylpyridine-3,5-dicarbothioate (dithiopyr), N'-(3,4-dichlorophenyl)-N,N-dimethylurea (diuron), N-(4-methylphenyl)-N'-(1-methyl-1-phenylethyl)urea (dymron, daimuron), 2-[2-(3-chlorophenyl)oxiranylmethyl]-2-ethyl-1H-indene-1,3(2H)-dione (epropodan), S-ethyl dipropylthiocarbamate (EPTC), S-(phenylmethyl)-N-ethyl-N-(1,2-dimethylpropyl)thiocarbamate (esprocarb), N-ethyl-N-(2-methyl-2-propenyl)-2,6-dinitro-4-trifluoromethylbenzeneamine (ethalfluralin), (S)-(2-ethoxy-1-methyl-2-oxoethyl) 2-chloro-5-(2-chloro-4-trifluoromethylphenoxy)benzoate (ethoxyfen), N-(4,6-dimethoxypyrimidin-2-yl)-N'-(2-ethoxyphenoxysulphonyl)urea (ethoxysulfuron), N-(2,3-dichlorophenyl)-4-ethoxymethoxybenzamide (etobenzanid), (R)-ethyl 2-[4-(6-chlorobenzoxazol-2-yloxy)phenoxy]propanoate (fenoxaprop-(P)-ethyl), isopropyl N-benzoyl-N-(3-chloro-4-fluorophenyl)-DL-alaninate (flamprop-isopropyl), isopropyl N-benzoyl-N-(3-chloro-4-fluorophenyl)-L-alaninate (flamprop-isopropyl-L), methyl N-benzoyl-N-(3-chloro-4-fluorophenoxy)-DL-alaninate (flamprop-methyl), N-(2,6-difluorophenyl)-8-fluoro-5-methoxy-[1,2,4]-triazolo-[1,5-c]-pyrimidine-2-sulphonamide (florasulam), (R)-butyl 2-[4-(5-trifluoromethylpyridin-2-yloxy)phenoxy]-propanoate (fluazifop, -butyl, -P-butyl), i-propyl 5-(4-bromo-1-methyl-5-trifluoromethyl-1H-pyrazol-3-yl)-2-chloro-4-fluorobenzoate (fluazolate), 4,5-dihydro-3-methoxy-4-methyl-5-oxo-N-[(2-trifluoromethoxyphenyl)sulphonyl]-1-H-1,2,4-triazole-1-carboxamide sodium salt (flucarbazone-sodium), N-(4-fluorophenyl)-N-i-propyl-2-(5-trifluoromethyl-1,3,4-thiadiazol-2-yloxy)acetamide (flufenacet), N-(2,6-difluorophenyl)-5-methyl-1,2,4-triazolo[1,5-a]-pyrimidine-2-sulphonamide (flumetsulam), pentyl [2-chloro-4-fluoro-5-(1,3,4,5,6,7-hexahydro-1,3-dioxo-2H-isoindol-2-yl)phenoxy]acetate (flumiclorac-pentyl), 2-[7-fluoro-3,4-dihydro-3-oxo-4-(2-propynyl)-2H-1,4-benzoxazin-6-yl]4,5,6,7-tetrahydro-1H-isoindole-1,3-ione (flumioxazin), 2-[4-chloro-2-fluoro-5-[(1-methyl-2-propynyl)oxy]phenyl]-4,5,6,7-tetrahydro-1H-isoindole-1,3(2H)-dione (flumipropyn), 3-chloro-4-chloromethyl-1-(3-trifluoromethylphenyl)-2-pyrrolidinone (fluorochloridone), ethoxycarbonylmethyl 5-(2-chloro-4-trifluoromethylphenoxy)-2-nitrobenzoate (fluoroglycofen-ethyl), 1-(4-chloro-3-(2,2,3,3,3-pentafluoropropoxymethyl)phenyl)-5-phenyl-1H-1,2,4-triazol-3-carboxamide (flupoxam), 1-isopropyl-2-chloro-5-(3,6-dihydro-3-methyl-2,6-dioxo-4-trifluoromethyl-1(2H)-pyrimidyl)benzoate (flupropacil), N-(4,6-dimethoxypyrimidin-2-yl)-N'-(3-methoxycarbonyl-6-trifluoromethylpyridin-2-ylsulphonyl)urea sodium salt (flupyrsulfuron-methyl-sodium), 9-hydroxy-9H-fluorene-9-carboxylic acid (flurenol), (4-amino-3,5-dichloro-6-fluoropyridin-2-yloxy)acetic acid (2-butoxy-1-methylethyl ester, 1-methyl-heptyl ester) (fluroxypyr, -butoxypropyl, -meptyl), 5-methylamino-2-phenyl-4-(3-trifluoromethylphenyl)-3(2H)-furanone (flurtamone), methyl [(2-chloro-4-fluoro-5-(tetrahydro-3-oxo-1H,3H-[1,3,4]-thiadiazolo-[3,4-a]-pyridazin-1-ylidene)aminophenyl]thioacetate (fluthiacet-methyl), 5-(2-chloro-4-trifluoromethylphenoxy)-N-methylsulphonyl-2-nitrobenzamide (fomesafen), 2-[[[[(4,6-dimethoxy-2-pyrimidinyl)amino]carbonyl]amino]sulphonyl]-4-formylamino-N,N-dimethylbenzamide (foramsulfuron), 2-amino-4-(hydroxymethylphosphinyl)butanoic acid (ammonium salt) (glufosinate (ammonium)), N-phosphonomethylglycine (isopropylammonium salt), (glyphosate, isopropylammonium), (R)-2-[4-(3-chloro-5-trifluoromethylpyridin-2-yl-oxy)phenoxy]propanoic acid (methyl ester, 2-ethoxyethyl ester, butyl ester) (haloxyfop, -methyl, -P-methyl, -ethoxyethyl, -butyl), 3-cyclohexyl-6-dimethylamino-1-methyl-1,3,5-triazine-2,4(1H,3H)-dione (hexazinone), methyl 2-(4,5-dihydro-4-methyl-4-isopropyl-5-oxo-1H-imidazol-2-yl)-4-methylbenzoate (imazamethabenz-methyl), 2-(4,5-dihydro-4-methyl-4-isopropyl-5-oxo-1H-imidazol-2-yl)-5-methylpyridine-3-carboxylic acid (imazamethapyr), 2-(4,5-dihydro-4-methyl-4-isopropyl-5-oxo-1H-imidazol-2-yl)-5-methoxymethylpyridine-3-carboxylic acid (imazamox), 2-(4,5-dihydro-4-methyl-4-isopropyl-5-oxo-1H-imidazol-2-yl)-quinoline-3-carboxylic acid (imazaquin), 2-(4,5-dihydro-4-methyl-4-i-propyl-5-oxo-1H-imidazol-2-yl)-5-ethylpyridine-3-carboxylic acid (imazethapyr), N-(4,6-dimethoxypyrimidin-2-yl)-N'-(2-chloro-imidazo[1,2-a]-pyridin-3-ylsulphonyl)urea (imazosulfuron), N-(4-methoxy-6-methyl-1,3,5-triazin-2-yl)-N'-(5-iodo-2-methoxycarbonylphenylsulphonyl)urea sodium salt (iodosulfuron-methyl-sodium), 4-hydroxy-3,5-diiodobenzonitrile (ioxynil), N,N-dimethyl-N'-(4-isopropylphenyl)urea (isoproturon), N-(3-(1-ethyl-1-methylpropyl)-isoxazol-5-yl)-2,6-dimethoxybenzamide (isoxaben), (4-chloro-2-methylsulphonyl-phenyl)-(5-cyclopropyl-isoxazol-4-yl)methanone (isoxachlortole), (5-cyclopropylisoxazol-4-yl)(2-methylsulphonyl-4-trifluoromethylphenyl)methanone (isoxaflutole), 2-[2-[4-[3,5-dichloro-2-pyridinyl)oxy]phenoxy]-1-oxo-propyl]isoxazolidine (isoxapyrifop), (2-ethoxy-1-methyl-2-oxoethyl) 5-(2-chloro-4-trifluoromethylphenoxy)-2-nitrobenzoate (lactofen), N'-(3,4-dichlorophenyl)-N-methoxy-N-methylurea (linuron), (4-chloro-2-methylphenoxy)acetic acid (MCPA), 2-(4-chloro-2-methylphenoxy)propionic acid (mecoprop), 2-(2-benzothiazolyloxy)-N-methyl-N-phenylacetamide (mefenacet), methyl 2-[[[[(4,6-dimethoxy-2-pyrimidinyl)amino]carbonyl]amino]sulphonyl]-4-[[(methylsulphonyl)amino]methyl]benzoate (mesosulfuron), 2-(4-methylsulphonyl-2-nitrobenzoyl)-1,3-cyclohexanedione (mesotrione), 4-amino-3-methyl-6-phenyl-1,2,4-triazin-5(4H)-one (metamitron), 2-chloro-N-(2,6-dimethylphenyl)-N-(1H-pyrazol-1-ylmethyl)acetamide (metazachlor), N'-(4-(3,4-dihydro-2-methoxy-2,4,4-trimethyl-2H-1-benzopyran-7-yl-oxy)phenyl)-N-methoxy-N-methylurea (metobenzuron), N'-(4-bromophenyl)-N-methoxy-N-methylurea (metobromuron), (S)-2-chloro-N-(2-ethyl-6-methylphenyl)-N-(2-methoxy-1-methylethyl)acetamide (metolachlor, S-metolachlor), N-(2,6-dichloro-3-methylphenyl)-5,7-dimethoxy-1,2,4-triazolo[1,5-a]-pyrimidine-2-sulphonamide (metosulam), N'-(3-chloro-4-methoxyphenyl)-N,N-dimethylurea (metoxuron), 4-amino-6-tert-butyl-3-methylthio-1,2,4-triazin-5(4H)-one (metribuzin), N-(4-methoxy-6-methyl-1,3,5-triazin-2-yl)-N'-(2-methoxycarbonylphenylsulphonyl)urea (metsulfuron-methyl), S-ethyl hexahydro-1H-azepin-1-carbothioate (molinate), 2-(2-naphthyloxy)-N-phenylpropanamide (naproanilide), N-butyl-N'-(3,4-dichlorophenyl)-N-methylurea (neburon), N-(4,6-dimethoxypyrimidin-2-yl)-N'-(3-dimethylcarbamoylpyridin-2-yl-sulphonyl)urea (nicosulfuron), 4-chloro-5-methylamino-2-(3-trifluoromethylphenyl)-3(2H)pyridazinone (norflurazon), S-(2-chlorobenzyl) N,N-diethylthiocarbamate (orbencarb), 4-dipropylamino-3,5-dinitrobenzenesulphonamide (oryzalin), 3-[2,4-dichloro-5-(2-propynyloxy)phenyl]-5-(t-butyl)-1,3,4-oxadiazol-2(3H)one (oxadiargyl), 3-[2,4-dichloro-5-(1-methylethoxy)-phenyl]-5-(t-butyl)-1,3,4- oxadiazol-2(3H)one (oxadiazon), N-(4,6-dimethylpyrimidin-2-yl)-N'-(2-oxetan-3-yloxycarbonylphenylsulphonyl)urea (oxasulfuron), 3-[1-(3,5-dichlorophenyl)-1-i-propyl]-2,3-dihydro-6-methyl-5-phenyl-4H-1,3-oxazin-4-one (oxaziclomefone), 2-chloro-1-(3-ethoxy-4-nitrophenoxy)-4-trifluoromethylbenzene (oxyfluorfen), 1,1'-dimethyl-4,4'-bipyridinium (paraquat), 1-amino-N-(1-ethylpropyl)-3,4-dimethyl-2,6-dinitrobenzene (pendimethalin), 4-(t-butyl)-N-(1-ethylpropyl)-2,6-dinitrobenzeneamine (pendralin), 3-(4-chloro-5-cyclopentyloxy-2-fluorophenyl)-5-(1-methylethylidene)-2,4-oxazolidinedione (pentoxazone), 4-amino-3,5,6-trichloropyridine-2-carboxylic acid (picloram), N-(4-fluorophenyl)-6-(3-trifluoromethylphenoxy)pyridine-2-carboxamide (picolinafen), S-[2-(2-methyl-1-piperidinyl)-2-oxoethyl]O,O-dipropyl phosphorodithioate (piperophos), 2-chloro-N-(2,6-diethylphenyl)-N-(2-propoxyethyl)acetamide (pretilachlor), N-(4,6-bis-difluoromethoxypyrimidin-2-yl)-N'-(2-methoxycarbonyl-phenylsulphonyl)urea (primisulfuron-methyl), 1-chloro-N-[2-chloro-4-fluoro-5-[(6S,7aR)-6-fluorotetrahydro-1,3-dioxo-1H-pyrrolo[1,2-c]imidazol-2(3H)-yl]phenyl]methanesulphonamide (profluazol), 2-chloro-N-isopropyl-N-phenylacetamide (propachlor), N-(3,4-dichlorophenyl)propanamide (propanil), (R)-[2-[[(1-methylethylidene)amino]oxy]ethyl]2-[4-(6-chloro-2-quinoxalinyloxy)phenoxy]propanoate (propaquizafop), 2-chloro-N-(2-ethyl-6-methylphenyl)-N-[(1-methylethoxy)methyl]acetamide (propisochlor), methyl 2-[[[(4,5-dihydro-4-methyl-5-oxo-3-propoxy-1H-1,2,4-triazol-1-yl)carbonyl]amino]-sulphonyl]benzoate sodium salt (propoxycarbazone-sodium), S-phenylmethyl-N,N-dipropylthiocarbamate (prosulfocarb), N-(4-methoxy-6-methyl-1,3,5-triazin-2-yl)-N'-(2-(3,3,3-trifluoropropyl)phenylsulphonyl)urea (prosulfuron), ethyl [2-chloro-5-(4-chloro-5-difluoromethoxy-1-methyl-1H-pyrazol-3-yl)-4-fluorophenoxy]acetate (pyraflufen-ethyl), 1-(3-chloro-4,5,6,7-tetrahydropyrazolo[1,5-a]pyridin-2-yl)-5-(methyl-2-propynylamino)-1H-pyrazole-4-carbonitrile (pyraclonil, pyrazogyl), 4-(2,4-dichlorobenzoyl)-1,3-dimethyl-5-(4-methylphenylsulphonyloxy)pyrazole (pyrazolate), 4-(2,4-dichlorobenzoyl)-1,3-dimethyl-5-(phenylcarbonylmethoxy)pyrazole (pyrazoxyfen), N-(4,6-dimethoxypyrimidin-2-yl)-N'-(4-ethoxycarbonyl-1-methylpyrazol-5-ylsulphonyl)urea (pyrazosulfuron-ethyl), diphenylmethanone O-[2,6-bis-(4,6-dimethoxypyrimidin-2-yloxy)benzoyl]oxime (pyribenzoxim), O-[3-(1,1-dimethyl-ethyl)phenyl](6-methoxy-2-pyridinyl)methylthiocarbamate (pyributicarb), 6-chloro-3-phenyl-4-pyridazinol (pyridafol), O-(6-chloro-3-phenylpyridazin-4-yl) S-octyl thiocarbonate (pyridate), 6-chloro-3-phenylpyridazin-4-ol (pyridatol), 7-[(4,6-dimethoxy-2-pyrimidinyl)thio]-3-methyl-[(3H)-isobenzofuranone (pyriftalid), methyl 2-(4,6-dimethoxypyrimidin-2-yloxy)benzoate (pyriminobac-methyl), 2-chloro-6-(4,6-dimethoxypyrimidin-2-ylthio)benzoic acid sodium salt (pyrithiobac-sodium), 3,7-dichloroquinoline-8-carboxylic acid (quinchlorac), 7-chloro-3-methylquinoline-8-carboxylic acid (quinmerac), 2-[4-(6-chloro-2-quinoxalinyloxy)phenoxy]propanoic acid (ethyl ester, tetrahydro-2-furanylmethyl ester) (quizalofop, -ethyl, -P-ethyl, -P-tefuryl), N-(4,6-dimethoxypyrimidin-2-yl)-N'-(3-ethylsulphonylpyridin-2-ylsulphonyl)urea (rimsulfuron), 2-(1-ethoximinobutyl)-5-(2-ethylthiopropyl)-3-hydroxy-2-cyclohexen-1-one (sethoxydim), 6-chloro-2,4-bisethylamino-1,3,5-triazine (simazine), 2-(2-chloro-4-methylsulphonylbenzoyl)-cyclohexane-1,3-dione (sulcotrione), 2-(2,4-dichloro-5-methylsulphonylaminophenyl)-4-difluoromethyl-5-methyl-2,4-dihydro-3H-1,2,4-triazol-3-one (sulfentrazone), methyl 2-[[[[(4,6-dimethyl-2-pyrimidinyl)amino]carbonyl]amino]sulphonyl]benzoate (sulfometuron-methyl), N-phosphonomethylglycinetrimethylsulphonium (sulfosate), N-(4,6-dimethoxypyrimidin-2-yl)-N'-(2-ethylsulphonylimidazo[1,2-a]pyridine-3-sulphonamide (sulfosulfuron), 6-chloro-4-ethylamino-2-tert-butylamino-1,3,5-triazine (terbuthylazine), 2-tert-butylamino-4-ethylamino-6-methylthio-1,3,5-triazine (terbutryn), 2-chloro-N-(2,6-dimethylphenyl)-N-(3-methoxy-2-thienylmethyl)acetamide (thenylchlor), methyl 2-difluoromethyl-5-(4,5-dihydrothiazol-2-yl)-4-(2-methylpropyl)-6-trifluoromethylpyridine-3-carboxylate (thiazopyr), 6-(6,7-dihydro-6,6-dimethyl-3H,5H-pyrrolo[2,1-c]-1,2,4-thiadiazol-3-ylideneamino)-7-fluoro-4-(2-propynyl)-2H-1,4-benzoxazin-3(4H)-one (thidiazimin), N-(4-methoxy-6-methyl-1,3,5-triazin-2-yl)-N'-(2-methoxycarbonyl-thien-3-ylsulphonyl)urea (thifensulfuron-methyl), 2-(ethoximinopropyl)-3-hydroxy-5-(2,4,6-trimethylphenyl)-2-cyclohexen-1-one (tralkoxydim), S-(2,3,3-trichloro-2-propenyl) diisopropylcarbamothioate (triallate), N-(4-methoxy-6-methyl-1,3,5-triazin-2-yl)-N'-[2-(2-chloroethoxy)phenylsulphonyl]urea (triasulfuron), N-methyl-N-(4-methoxy-6-methyl-1,3,5-triazin-2-yl)-N'-(2-methoxycarbonylphenylsulphonyl)urea (tribenuron-methyl), (3,5,6-trichloro)pyridin-2-yloxyacetic acid (triclopyr), 2-(3,5-dichlorophenyl)-2-(2,2,2-trichloroethyl)oxirane (tridiphane), N-[[(4,6-dimethoxy-2-pyrimidinyl)amino]carbonyl]-3-(2,2,2-trifluoroethoxy)-2-pyridinesulphonamide sodium salt (trifloxysulfuron), 1-amino-2,6-dinitro-N,N-dipropyl-4-trifluoromethylbenzene (trifluralin), N-[4-dimethylamino-6-(2,2,2-trifluoroethoxy)-1,3,5-triazin-2-yl]-N'-(2-methoxycarbonylphenylsulphonyl)urea (triflusulfuron-methyl), N-(4-methoxy-6-trifluoromethoxy-1,3,5-triazin-2-yl)-N'-(2-trifluoromethylphenylsulphonyl)urea (tritosulfuron), N-[[(4,6-dimethoxy-2-pyrimidinyl)amino]carbonyl]-3-(N-methyl-N-methylsulphonylamino])-2-pyridine-sulphonamide, (cf. WO-A-91/10660), 4-[4,5-dihydro-4-methyl-5-oxo-(3-trifluoromethyl)-1H-1,2,4-triazol-1-yl]-2-(ethylsulphonylamino)-5-fluorobenzenecarbothioamide (cf. WO-95/30661), phenylcarbothiamide, 4-[4,5-dihydro-4-methyl-5-oxo-3-(trifluoromethyl)-1H-1,2,4-triazol-1-yl]-2-[(ethylsulphonyl)amino]-5-fluoro-(CAS No. 173980-17-1, HWH4991) and 2-chloro-N-[1-(2,6-dichloro-4-difluoromethylphenyl)-4-nitro-1H-pyrazol-5-yl]propanecarboxamide (CAS No. 121750-17-2; SLA5599).

Also preferably suitable for use as third or further active compounds are:

acetochlor
acetochlor + dichlormid
acetochlor + furilazole
acetochlor + R-29148
alachlor
amicarbazone
amidosulfuron
anilofos
anilofos + 2,4-D
anilofos + propanil
anilofos + quinoclamine
atrazine
azimsulfuron
azimsulfuron + dymron -continued azimsulfuron + anilofos
azimsulfuron + benfuresate
azimsulfuron + bensulfuron
azimsulfuron + butachlor
azimsulfuron + cafenstrole
azimsulfuron + cyhalofop-butyl
azimsulfuron + dimepiperate
azimsulfuron + esprocarb
azimsulfuron + mefenacet
azimsulfuron + indanofan
azimsulfuron + oxaziclomefone
azimsulfuron + pretilachlor
azimsulfuron + thenylchlor
azimsulfuron + anilofos + dymron
azimsulfuron + benfuresate + dymron
azimsulfuron + bensulfuron + cafenstrole
azimsulfuron + bensulfuron + cyhalofop-butyl
azimsulfuron + bensulfuron + dymron
azimsulfuron + bensulfuron + dimethametryn
azimsulfuron + bensulfuron + indanofan
azimsulfuron + bensulfuron + pretilachlor
azimsulfuron + bensulfuron + thenylchlor
azimsulfuron + butachlor + dymron
azimsulfuron + cafenstrole + dymron
azimsulfuron + cyhalofop-butyl + dymron
azimsulfuron + mefenacet + dymron
azimsulfuron + oxaziclomefone + dymron
azimsulfuron + pretilachlor + dymron
benfuresate
bensulfuron-methyl
bensulfuron-methyl + dymron
bensulfuron-methyl + anilofos
bensulfuron-methyl + benfuresate
bensulfuron-methyl + butachlor
bensulfuron-methyl + cafenstrole
bensulfuron-methyl + cyhalofop-butyl
bensulfuron-methyl + dimepiperate
bensulfuron-methyl + dithiopyr
bensulfuron-methyl + esprocarb
bensulfuron-methyl + indanofan
bensulfuron-methyl + mefenacet
bensulfuron-methyl + metsulfuron-methyl
bensulfuron-methyl + molinate
bensulfuron-methyl + oxaziclomefone
bensulfuron-methyl + pretilachlor
bensulfuron-methyl + pyributicarb
bensulfuron-methyl + quinclorac
bensulfuron-methyl + thenylchlor
bensulfuron-methyl + anilofos + dymron
bensulfuron-methyl + benfuresate + dymron
bensulfuron-methyl + butachlor + dymron
bensulfuron-methyl + benfuresate + dimepiperate
bensulfuron-methyl + benfuresate + pretilachlor
bensulfuron-methyl + cafenstrole + dymron
bensulfuron-methyl + cafenstrole + cyhalofop-butyl
bensulfuron-methyl + cyhalofop-butyl + dymron
bensulfuron-methyl + cyhalofop-butyl + thenylchlor
bensulfuron-methyl + dithiopyr + quinclorac
bensulfuron-methyl + mefenacet + dymron
bensulfuron-methyl + mefenacet + benthiocarb
bensulfuron-methyl + mefenacet + molinate
bensulfuron-methyl + oxaziclomefone + dymron
bensulfuron-methyl + pretilachlor + dymron
bensulfuron-methyl + pyributicarb + dymron
bentazone
bentazone + quinclorac
benthiocarb (thiobencarb)
benthiocarb + chlornitrofen
benthiocarb + propanil
benthiocarb + simetryn
benzobicyclon
benzofenap
benzofenap + thenylchlor + cumyluron
bifenox
bifenox + pretilachlor
bifenox + thenylchlor
bispyribac-sodium
bispyribac-sodium + benthiocarb
bromobutide -continued bromobutide + pyrazoxyfen
bromobutide + benzofenap + pyributicarb
bromobutide + bifenox + pyrazolate
bromobutide + pyrazoxyfen + thenylchlor
butachlor
butachlor + chlomethoxyfen
butachlor + oxadiazon
butachlor + propanil
butachlor + pyrazolate
butamifos
butamifos + bromobutide
butenachlor
cafenstrole
cafenstrole + dymron
cafenstrole + cyhalofop-butyl + dymron
carfentrazone-ethyl
chlomethoxyfen
chlornitrofen
chlornitrofen + dymron
cinmethylin
cinmethylin + 2,4-D
cinosulfuron
cinosulfuron + dymron
cinosulfuron + anilofos
cinosulfuron + benfuresate
cinosulfuron + butachlor
cinosulfuron + cafenstrole + dymron
cinosulfuron + cyhalofop-butyl
cinosulfuron + dimepiperate
cinosulfuron + esprocarb
cinosulfuron + mefenacet
cinosulfuron + mefenacet + dymron
cinosulfuron + molinate
cinosulfuron + oxaziclomefone
cinosulfuron + pretilachlor
cinosulfuron + pretilachlor + dymron
cinosulfuron + pretilachlor + fenclorim
cinosulfuron + pretilachlor + quinclorac
cinosulfuron + pyriftalid
clefoxydim
clodinafop-propargyl
clodinafop-propargyl + cloquintocet-mexyl
clomazone
clomazone + propanil
clomeprop
clomeprop + pretilachlor
cumyluron
cyanazine
cyclosulfamuron
cyclosulfamuron + dymron
cyclosulfamuron + anilofos
cyclosulfamuron + benfuresate
cyclosulfamuron + butachlor
cyclosulfamuron + cafenstrole + dymron
cyclosulfamuron + cyhalofop-butyl
cyclosulfamuron + dimepiperate
cyclosulfamuron + esprocarb
cyclosulfamuron + mefenacet
cyclosulfamuron + mefenacet + dymron
cyclosulfamuron + oxaziclomefone
cyclosulfamuron + pentoxazone
cyclosulfamuron + pretilachlor
cyclosulfamuron + quinclorac
cyhalofop-butyl
cyhalofop-butyl + bentazon
2,4-D
dichlorprop-P
diethatyl-ethyl
dimepiperate
dimethametryn
dimethametryn + piperophos
dimethenamid
S-dimethenamid
dithiopyr
dymron
esprocarb
ethoxysulfuron
ethoxysulfuron + dymron
ethoxysulfuron + anilofos -continued ethoxysulfuron + anilofos + dymron
ethoxysulfuron + benfuresate
ethoxysulfuron + anilofos + benfuresate
ethoxysulfuron + benfuresate + dymron
ethoxysulfuron + butachlor
ethoxysulfuron + cafenstrole
ethoxysulfuron + cafenstrole + dymron
ethoxysulfuron + cyhalofop-butyl
ethoxysulfuron + dimepiperate
ethoxysulfuron + esprocarb
ethoxysulfuron + mefenacet
ethoxysulfuron + mefenacet + dymron
ethoxysulfuron + oxaziclomefone
ethoxysulfuron + pretilachlor + dymron
ethoxysulfuron + pretilachlor + pyrazolate
etobenzanid
fenoxaprop-(P)-ethyl
fenoxaprop-(P)-ethyl + fenclorim
fenoxaprop-(P)-ethyl + isoxadifen-ethyl
fenoxaprop-(P)-ethyl + mefenpyr-diethyl
pentoxazone
bispyribac-sodium
bromobutide
benzofenap
clomeprop
dymron
flufenacet
oxaziclomefone
propanil
pyribenzoxim
pyriminobac-methyl
quinoclamine
azimsulfuron
azimsulfuron + dymron
azimsulfuron + bensulfuron-methyl
bensulfuron-methyl
bensulfuron-methyl + dymron
cinosulfuron
cinosulfuron + dymron
cyclosulfamuron
cyclosulfamuron + dymron
ethoxysulfuron
ethoxysulfuron + dymron
imazosulfuron
imazosulfuron + dymron
pyrazosulfuron-ethyl
pyrazosulfuron-ethyl + dymron
fluazifop-P-butyl
flucarbazone-sodium
flucarbazone-sodium + fenclorim
flucarbazone-sodium + isoxadifen-ethyl
flucarbazone-sodium + mefenpyr-diethyl
flufenacet
flufenacet + 2,4-D
flufenacet + diflufenican
flufenacet + metosulam
flufenacet + propanil
flufenacet + dichlormid
flufenacet + furilazole
flufenacet + R-29148
flufenacet + fenclorim
flufenacet + isoxadifen-ethyl
flufenacet + mefenpyr-diethyl
flumetsulam
halosulfuron-methyl
halosulfuron-methyl + cafenstrole + cyhalofop-butyl
halosulfuron-methyl + cafenstrole + dymron
halosulfuron-methyl + cyhalofop-butyl + dymron
haloxyfop-P-methyl
HOK-201
imazamox
imazaquin
imazethapyr
imazosulfuron
imazosulfuron + dymron
imazosulfuron + anilofos
imazosulfuron + benfuresate
imazosulfuron + butachlor
imazosulfuron + cafenstrole + dymron
imazosulfuron + cyhalofop-butyl
imazosulfuron + dimepiperate
imazosulfuron + dimethametryn
imazosulfuron + dimethametryn + pretilachlor
imazosulfuron + esprocarb + dymron
imazosulfuron + etobenzanid + Dymron
imazosulfuron + mefenacet + Dymron
imazosulfuron + oxaziclomefone
imazosulfuron + pentoxazone + dymron
imazosulfuron + pretilachlor + dymron
imazosulfuron + pyributicarb + dymron
indanofan
isoxaflutole
MCPA
mefenacet
mefenacet + molinate
mefenacet + quinoclamine
mefenacet + bromobutide + naproanilide
mesosulfuron
mesosulfuron + dymron
mesosulfuron + anilofos
mesosulfuron + benfuresate
mesosulfuron + cafenstrole + dymron
mesosulfuron + cyhalofop-butyl
mesosulfuron + dimepiperate
mesosulfuron + esprocarb
mesosulfuron + mefenacet
mesosulfuron + mefenacet + dymron
mesosulfuron + oxaziclomefone
mesosulfuron + pretilachlor
mesosulfuron + pyributicarb
mesotrione
metolachlor
metolachlor + benoxacor
S-metolachlor
S-metolachlor + benoxacor
metosulam
metsulfuron-methyl
metribuzin
molinate
molinate + propanil
molinate + simetryn
naproanilide
nicosulfuron
OK-701
oxadiargyl
oxadiargyl + propanil
oxadiazon
oxaziclomefone
oxyfluorfen
pendimethalin
pentoxazone
pentoxazone + cumyluron
piperophos
piperophos + 2,4-D
pretilachlor
pretilachlor + dimethametryn
pretilachlor + dymron
pretilachlor + dimethametryn + dymron
pretilachlor + fenclorim
profoxydim
propanil
propoxycarbazone-sodium
pyraclonil
pyrazolate
pyrazolate + butachlor
pyrazolate + pretilachlor
pyrazosulfuron-ethyl
pyrazosulfuron-ethyl + dymron
pyrazosulfuron-ethyl + indanofan
pyrazosulfuron-ethyl + etobenzanid
pyrazosulfuron-ethyl + esprocarb
pyrazosulfuron-ethyl + esprocarb + dimethametryn
pyrazosulfuron-ethyl + esprocarb + pretilachlor
pyrazosulfuron-ethyl + mefenacet
pyrazosulfuron-ethyl + molinate
pyrazosulfuron-ethyl + pentoxazone
pyrazosulfuron-ethyl + anilofos + dymron
pyrazosulfuron-ethyl + benfuresate + dymron -continued pyrazosulfuron-ethyl + butachlor + dymron
pyrazosulfuron-ethyl + cafenstrole
pyrazosulfuron-ethyl + cafenstrole + cyhalofop-butyl
pyrazosulfuron-ethyl + dimepiperate + dymron
pyrazosulfuron-ethyl + dithiopyr + esprocarb
pyrazosulfuron-ethyl + mefenacet + dymron
pyrazosulfuron-ethyl + oxaziclomefone + dymron
pyrazosulfuron-ethyl + pretilachlor
pyrazosulfuron-ethyl + pretilachlor + quinclorac
pyrazosulfuron-ethyl + thenylchlor
pyrazoxyfen
pyribenzoxim
pyributicarb
pyributicarb + pretilachlor
pyriftalid
pyriminobac-methyl
quinclorac
quinoclamine
simazine
simetryn
sulcotrione
terbuthylazine
thenylchlor
thifensulfuron-methyl
tiocarbazil
tritosulfuron The active compound combinations according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus* and *Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis* and *Cucurbita.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrosfis, Alopecurus, Apera* and *Phalaris.*

Monocotyledonous crops of the genera: *Oryza, Zea, Triticum, Hordeum, Avena, Secale, Sorghum, Panicum, Saccharum, Ananas, Asparagus* and *Allium.*

However, the use of the active compound combinations according to the invention is in no way restricted to these genera, but also extends in the same manner to other plants.

According to the invention, it is possible to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The synergistic effect of the active compound combinations according to the invention is particularly pronounced at certain concentration ratios. However, the ratios by weight of the active compounds in the active compound combinations can be varied within relatively wide ranges. In general, from 0.01 to 1000 parts by weight, preferably from 0.1 to 100 parts by weight and particularly preferably from 0.1 to 10 parts by weight of active compound of group 2 are present per part by weight of the active compound of the formula (I).

The advantageous effect of the crop plant compatibility of the active compound combinations according to the invention is likewise particularly strongly pronounced at certain concentration ratios. However, the ratios by weight of the active compounds in the active compound combinations can be varied within relatively wide ranges. In general, from 0.001 to 1000 parts by weight preferably from 0.01 to 100 parts by weight and particularly preferably from 0.1 to 10 parts by weight of one of the compounds, mentioned above under (c), which improve compatibility with crop plants (antidotes/safeners) are present per part by weight of active compound of the formula (I) or its mixtures with active compounds of group 2.

The active compound combinations can be converted into the customary formulations, such as solutions, emulsions, wettable powders, suspensions, powders, dusts, pastes, soluble powders, granules, suspo-emulsion concentrates, natural and synthetic substances impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water it is also possible to use, for example, organic solvents as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable Solid Carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as protein hydrolysates; suitable dispersing agents are: for example lignosulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight, preferably between 0.5 and 90%, of active compounds.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomising, dusting or scattering.

The active compound combinations according to the invention can be applied before and after the plants have emerged, that is to say pre-emergence and post-emergence. They can also be incorporated into the soil before sowing.

A synergistic effect in herbicides is always present when the herbicidal activity of the active compound combination exceeds the activity of the active compounds when applied individually.

The expected activity for a given combination of two herbicides can be calculated as follows (cf. COLBY, S. R.: "Calculating synergistic and antagonistic responses of herbicide combinations", Weeds 15, pages 20–22, 1967):

If $X$=% damage by herbicide A (active compound of the formula I) at an application rate of p kg/ha
and $Y$=% damage by herbicide B (active compound of the formula II) at an application rate of q kg/ha
and $E$=the expected damage of the herbicides A and B at application rates of p and q kg/ha,
then $E=X+Y-(X*Y/100)$.

If the actual damage exceeds the calculated value, then the activity of the combination is superadditive, i.e. a synergistic effect exists.

USE EXAMPLES

Example A

Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 10 days after sowing (when the rice has reached the 1-2-leaf stage), the spray preparation is applied to the test areas (using a hand-operated sprayer). 1 month after the treatment, the soil is flooded to a water depth of 5 cm; the standing water levels are kept constant.

3 weeks after the active compound application, the degree of damage to the rice plants and the herbicidal effect on the emerged weeds of the species *Aeschynomene rudis* is scored visually in percent in comparison to an untreated control.

The figures denote:

0%=no action/damage (like untreated control)
100%=total destruction

The results are shown in the table below.

TABLE A-1

| Active compound or combination | Application rate g/ha (active compound) | Test plants Damage or action in % | | | |
|---|---|---|---|---|---|
| | | *Aeschynomene rudis* | | Paddy rice (*Oryza* sp.) | |
| | | found | calc. | found | calc. |
| (A) -known- | 400 | 30 | | 0 | |
| (B) -known- | 40 | 90 | | 0 | |
| (A) + (B) -according to the invention- | 400 + 40 | 95 | (93) | 0 | | calc. = calculated
A fentrazamide 250 EC 400 g a.i./ha
B bispyribac-sodium 400 SC 40 g a.i./ha
A + B fentrazamide 250 EC + Bispyribac-sodium 400 SC 400 + 40 g a.i./ha
Outdoor test in sown rice (Brazil 1999)
Spray application during the 1–2-leaf stage of the rice Example B Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 29 days after sowing (during the BBCH 23 development stage of the rice; begin of stocking), the spray preparation is applied to the test areas (using a hand-operated sprayer). A few days after the treatment, the soil is flooded to a water depth of 5 cm; the standing water levels are kept constant.

2 weeks after the active compound application, the degree of damage to the rice plants and the herbicidal effect on the emerged weeds *Echinochloa crus-galli* and *Brachiaria plantaginea* is scored visually in percent in comparison to an untreated control.

The figures denote:

0%=no action/damage (like untreated control)

100%=total destruction

The results are shown in the table below.

TABLE B-1

| Active compound or combination | Application rate g/ha (active compound) | Test plants Damage or action in % | | | | | |
|---|---|---|---|---|---|---|---|
| | | *Echinochloa crus-galli* | | *Brachiaria plantaginea* | | Paddy rice (*Oryza* sp.) | |
| | | found | calc. | found | calc. | found | calc. |
| (A) -known- | 300 | 35 | | 10 | | 0 | |
| (B) -known- | 75 | 70 | | 85 | | 8 | |
| (A) + (B) -according to the invention- | 300 + 75 | 90 | (80.5) | 93 | (86.5) | 10 | | calc. = calculated
A fentrazamide 250 EC 300 g a.i./ha
B profoxydim 200 EC 75 g a.i./ha
A + B fentrazamide 250 EC + profoxydim 200 EC 300 + 75 g a.i./ha
Outdoor test in sown rice (Brazil 1999)
Spray application during the BBCH 23 stage of the rice (begin of stocking)

Example C

Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 29 days after sowing (during the BBCH 23 development stage of the rice; begin of stocking), the spray preparation is applied to the test areas (using a hand-operated sprayer). A few days after the treatment, the soil is flooded to a water depth of 5 cm; the standing water levels are kept constant.

2 weeks after the active compound application, the degree of damage to the rice plants and the herbicidal effect on the emerged weeds *Echinochloa crus-galli* and *Brachiaria plantaginea* is scored visually in percent in comparison to an untreated control.

The figures denote:

0%=no action/damage (like untreated control)

100%=total destruction

The results are shown in the table below.

TABLE C-1

| Active compound or combination | Application rate g/ha (active compound) | Test plants Damage or action in % | | | | | |
|---|---|---|---|---|---|---|---|
| | | *Echinochloa crus-galli* | | *Brachiaria plantaginea* | | Paddy rice (*Oryza* sp.) | |
| | | found | calc. | found | calc. | found | calc. |
| (A) -known- | 300 | 35 | | 10 | | 0 | |
| (B) -known- | 75 | 70 | | 85 | | 8 | |
| (A) + (B) -according to the invention- | 150 + 75 | 85 | (80.5) | 90 | (86.5) | 10 | | calc. = calculated
A fentrazamide 250 EC 300 g a.i./ha
B profoxydim 200 EC 75 g a.i./ha
A + B fentrazamide 250 EC + profoxydim 200 EC 150 + 75 g a.i./ha
Outdoor test in sown rice (Brazil 1999)
Spray application during the BBCH 23 stage of the rice (begin of stocking)

Example D

Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 29 days after sowing (during the BBCH 23 development stage of the rice; begin of stocking), the spray preparation is applied to the test areas (using a hand-operated sprayer). A few days after the treatment, the soil is flooded to a water depth of 5 cm; the standing water levels are kept constant.

2 weeks after the active compound application, the degree of damage to the rice plants and the herbicidal effect on the emerged weeds *Echinochloa crus-galli* and *Brachiaria plantaginea* is scored visually in percent in comparison to an untreated control.

The figures denote:

0%=no action/damage (like untreated control)

100%=total destruction

The results are shown in the table below.

TABLE D-1

| Active compound or combination | Application rate g/ha (active compound) | Test plants Damage or action in % | | | | | |
|---|---|---|---|---|---|---|---|
| | | *Echinochloa crus-galli* | | *Brachiaria plantaginea* | | Paddy rice (*Oryza* sp.) | |
| | | found | calc. | found | calc. | found | calc. |
| (A) -known- | 300 | 35 | | 10 | | 0 | |
| (B) -known- | 100 | 75 | | 80 | | 10 | |

TABLE D-1-continued

| Active compound or combination | Application rate g/ha (active compound) | Test plants Damage or action in % | | | | | |
|---|---|---|---|---|---|---|---|
| | | *Echinochloa crus-galli* | | *Brachiaria plantaginea* | | Paddy rice (*Oryza* sp.) | |
| | | found | calc. | found | calc. | found | calc. |
| (A) + (B) -according to the invention- | 300 + 100 | 85 | (83) | 93 | (82) | 10 | | calc. = calculated
A fentrazamide 250 EC 300 g a.i./ha
B profoxydim 200 EC 100 g a.i./ha
A + B fentrazamide 250 EC + profoxydim 200 EC 300 + 100 g a.i./ha
Outdoor test in sown rice (Brazil 1999)
Spray application during the BBCH 23 stage of the rice (begin of stocking)

Example E

Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 29 days after sowing (during the BBCH 23 development stage of the rice; begin of stocking), the spray preparation is applied to the test areas (using a hand-operated sprayer). A few days after the treatment, the soil is flooded to a water depth of 5 cm; the standing water levels are kept constant.

2 weeks after the active compound application, the degree of damage to the rice plants and the herbicidal effect on the emerged weeds *Echinochloa crus-galli* and *Brachiaria plantaginea* is scored visually in percent in comparison to an untreated control.

The figures denote:
0%=no action/damage (like untreated control)
100%=total destruction The results are shown in the table below.

TABLE E-1

| Active compound or combination | Application rate g/ha (active compound) | Test plants Damage or action in % | | | | | |
|---|---|---|---|---|---|---|---|
| | | *Echinochloa crus-galli* | | *Brachiaria plantaginea* | | Paddy rice (*Oryza* sp.) | |
| | | found | calc. | found | calc. | found | calc. |
| (A) -known- | 300 | 35 | | 10 | | 0 | |
| (B) -known- | 100 | 75 | | 80 | | 10 | |
| (A) + (B) -according to the invention- | 150 + 100 | 85 | (83) | 90 | (82) | 13 | | calc. = calculated
A fentrazamide 250 EC 300 g a.i./ha
B profoxydim 200 EC 100 g a.i./ha
A + B fentrazamide 250 EC + profoxydim 200 EC 150 + 100 g a.i./ha
Outdoor test in sown rice (Brazil 1999)
Spray application during the BBCH 23 stage of the rice (begin of stocking)

Example F

Test in Sown Rice (Brazil)

To prepare a spray preparation, the active compound preparations are mixed with water. The concentration is adjusted so that the application rate corresponds to 200 l of water/ha.

Rice seeds are sown in test plots (2 m×5 m) in rice paddies. 18 days after sowing (during the BBCH 12 development stage of the rice; corresponds to the 2-leaf-stage), the spray preparation is applied to the test areas (using a hand-operated sprayer).

3 weeks after the active compound application, the degree of damage to the rice plants and the herbicidal effect on the emerged weeds *Acanthospermum hispidum, Commelina benghalensis, Digitaria sanguinalis* and *Eleusine indica* is scored visually in percent in comparison to an untreated control.

The figures denote:
0%=no action/damage (like untreated control)
100%=total destruction
The results are shown in the table below.

TABLE F-1

| Active compound or combination | Application rate g/ha (active compound) | Test plants Damage or action in % | | | | | | | | |
|---|---|---|---|---|---|---|---|---|---|---|
| | | *Acantho-spermum hispidum* | | *Commelina Bengha-lensis* | | *Digitaria Sanguina-lis* | | *Eleusine indica* | | Mountain rice (*Oryza* sp.) |
| | | found | calc. | found | calc. | found | calc. | found | calc. | found calc. |
| (A) -known- | 300 | 50 | | 50 | | 50 | | 50 | | 0 |
| (B) -known- | 100 | 40 | | 40 | | 50 | | 50 | | 0 |
| (A) + (B) -according to the invention- | 150 + 100 | 80 | (70) | 80 | (70) | 80 | (75) | 80 | (75) | 0 | calc. = calculated
A fentrazamide 250 EC 300 g a.i./ha
B profoxydim 200 EC 100 g a.i./ha
A + B fentrazamide 250 EC + profoxydim 200 EC 150 + 100 g a.i./ha
Outdoor test in sown rice (Brazil 1999)
Spray application during the BBCH 12 stage of the rice (2-leaf-stage)

Example G

Test in Sown Rice (Philippines)

To prepare a spray preparation, the active compound preparations are mixed with water. The concentration is adjusted so that the application rate corresponds to 200 l of water/ha.

Rice seeds are sown in test plots (2.5 m×2.5 m) in rice paddies. 11 days after sowing (4-leaf-stage of the rice), the spray preparation is applied to the test areas (using a hand-operated sprayer). 1 day after the treatment, the soil is flooded to a water depth of 5 cm; the standing water levels are kept constant.

8 weeks after the active compound application, the degree of damage to the rice plants and the herbicidal effect on the emerged weeds of the species *Echinochloa crus-galli* is scored visually in percent in comparison to an untreated control.

The figures denote:
0%=no action/damage (like untreated control)
100%=total destruction
The results are shown in the table below.

TABLE G-1

| Active compound or combination | Application rate g/ha (active compound) | Test plants Damage or action in % | | | |
|---|---|---|---|---|---|
| | | *Echinochloa crus-galli* | | Paddy rice (*Oryza* sp.) | |
| | | found | calc. | found | calc. |
| (A) -known- | 135 | 78 | | 0 | |
| (B) -known- | 75 | 50 | | 0 | |
| (A) + (B) -according to the invention- | 135 + 75 | 93 | (89) | 2 | | calc. = calculated
A fentrazamide 50 WP 135 g a.i./ha
B profoxydim 200 EC 75 g a.i./ha
A + B fentrazamide 50 WP + profoxydim 200 EC 135 + 75 g a.i./ha
Outdoor test in sown rice (Philippines 1999)
Spray application 11 days after sowing

Example H

Test in Sown Rice (Thailand)

To prepare a spray preparation, the active compound preparations are mixed with water. The concentration is adjusted so that the application rate corresponds to 200 l of water/ha.

Rice seeds are sown in test plots (2.5 m×2.5 m) in rice paddies. 7 days after sowing (2-leaf-stage of the rice), the spray preparation is applied to the test areas (using a hand-operated sprayer). 2 days after the treatment, the soil is flooded to a water depth of 5 cm; the standing water levels are kept constant.

8 weeks after the active compound application, the degree of damage to the rice plants and the herbicidal effect on the emerged weeds *Echinochloa crus-galli* and *Leptochloa chinensis* is scored visually in percent in comparison to an untreated control.

The figures denote:
0%=no action/damage (like untreated control)
100%=total destruction
The results are shown in the table below.

TABLE H-1

| Active compound or combination | Application rate g/ha (active compound) | Test plants Damage or action in % | | | | | |
|---|---|---|---|---|---|---|---|
| | | *Echinochloa crus-galli* | | *Leptochloa chinensis* | | Paddy rice (*Oryza* sp.) | |
| | | found | calc. | found | calc. | found | calc. |
| (A) -known- | 135 | 47 | | 38 | | 3 | |
| (B) -known- | 50 | 60 | | 63 | | 0 | |
| (A) + (B) -according to- the invention- | 135 + 50 | 85 | (79) | 85 | (77) | 5 | | calc. = calculated
A fentrazamide 50 WP 135 g a.i./ha
B profoxydim 200 EC 50 g a.i./ha
A + B fentrazamide 50 WP + profoxydim 200 EC 135 + 50 g a.i./ha
Outdoor test in sown rice (Thailand 1999)
Spray application 7 days after sowing

Example I

Test in Sown Rice (Thailand)

To prepare a spray preparation, the active compound preparations are mixed with water. The concentration is adjusted so that the application rate corresponds to 200 l of water/ha.

Rice seeds are sown in test plots (2.5 m×2.5 m) in rice paddies. 7 days after sowing (2-leaf-stage of the rice), the spray preparation is applied to the test areas (using a hand-operated sprayer). 2 days after the treatment, the soil is flooded to a water depth of 5 cm; the standing water levels are kept constant.

3 weeks after the active compound application, the degree of damage to the rice plants and the herbicidal effect on the emerged weeds *Echinochloa crus-galli* is scored visually in percent in comparison to an untreated control.

The figures denote:
0%=no action/damage (like untreated control)
100%=total destruction
The results are shown in the table below.

TABLE I-1

| Active compound or combination | Application rate g/ha (active compound) | Test plants Damage or action in % | | | |
|---|---|---|---|---|---|
| | | *Echinochloa crus-galli* | | Paddy rice (*Oryza* sp.) | |
| | | found | calc. | found | calc. |
| (A) -known- | 135 | 58 | | 2 | |
| (B) -known- | 50 | 63 | | 0 | |
| (A) + (B) -according to the invention- | 135 + 50 | 92 | (84) | 6 | | calc. = calculated
A fentrazamide 50 WP 135 g a.i./ha
B profoxydim 200 EC 50 g a.i./ha
A + B fentrazamide 50 WP + profoxydim 200 EC 135 + 50 g a.i./ha
Outdoor test in sown rice (Thailand 1999)
Spray application 7 days after sowing

What is claimed is:

1. A composition comprising an effective amount of an active compound combination comprising (a) the compound 4-(2-chlorophenyl)-N-cyclohexyl-N-ethyl-4,5-dihydro-5-oxo-1H-tetrazole-1-carboxamide (fentrazamide) of formula (I)

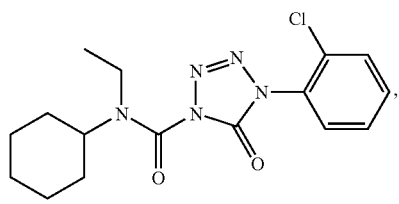

and (b) one or more compounds selected from a second group of herbicides consisting of 2,6-bis[(4,6-dimethoxy-2-pyrimidinyl)oxy]benzoic acid (bispyribac) and its salts, diphenylmethanone O-[2,6-bis[(4,6-dimethoxy-2-pyrimidinyl)oxy]-benzoyl]oxime (pyribenzoxim), and 2-[1-[[2-(4-chlorophenoxy)propoxy]amino]butyl]-5-(tetrahydro-2H-thiopyran-3-yl)-1,3-cyclohexanedione (profoxydim);

and, optionally, (c) one or more compounds that improves crop plant compatibility selected from the group consisting of the compounds α-(1,3-dioxolan-2-ylmethoximino)-phenylacetonitrile (oxabetrinil), α-(cyanomethoximino)phenylacetonitrile (cyometrinil), 4-chloro-N-(1,3-dioxolan-2-ylmethoxy)-α-trifluoroacetophenone oxime (fluxofenim), 4,6-dichloro-2-phenylpyrimidine (fenclorim), 4-dichloroacetyl-3,4-dihydro-3-methyl-2H-1,4-benzoxazine (benoxacor), 1-methylhexyl 5-chloroquinoxaline-8-oxyacetate (cloquintocet), 2,2-dichloro-N-(2-oxo-2-(2-propenylamino)ethyl)-N-(2-propenyl)acetamide (DKA-24), 1,8-naphthalic anhydride, ethyl 1-(2,4-dichlorophenyl)-5-trichloromethyl-1H-1,2,4-triazole-3-carboxylate (fenchlorazole ethyl), phenylmethyl 2-chloro-4-trifluoromethylthiazole-5-carboxylate (flurazole), 3-dichloroacetyl-5-(2-furanyl)-2,2-dimethyloxazolidine (furilazole, MON-13900), 4-dichloroacetyl-1-oxa-4-azaspiro[4.5]-decane (AD-67), 2-dichloromethyl-2-methyl-1,3-dioxolane (MG-191), 2,2-dichloro-N-(1,3-dioxolan-2-ylmethyl)-N-(2-propenyl)acetamide (PPG-1292), 2,2-dichloro-N,N-di-2-propenylacetamide (dichlormid), N-(4-methylphenyl)-N'-(1-methyl-1-phenylethyl)urea (dymron), 1-dichloroacetylhexahydro-3,3,8a-trimethylpyrrolo[1,2-a]pyrimidin-6(2H)one (BAS-145138), N-(2-methoxybenzoyl)-4-(methylaminocarbonylamino)benzenesulphonamide, ethyl 4,5-dihydro-5,5-diphenyl-3-isoxazolecarboxylate (isoxadifen-ethyl), (4-chloro-2-methylphenoxy)acetic acid (MCPA), 2-(4-chloro-2-methylphenoxy)propionic acid (mecoprop), diethyl-1-(2,4-dichlorophenyl)-4,5-dihydro-5-methyl-1H-pyrazol-3,5-dicarboxylate (mefenpyr-diethyl) and 2,4-dichlorophenoxyacetic acid (2,4-D) and its derivatives, 4-(2-chlorobenzoylaminosulphonyl)-N-propyl-benzamide, N-(phenylsulphamoyl)benzamide derivatives of formula (II)

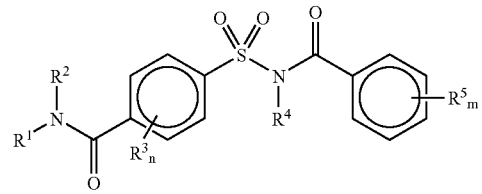

in which

R¹ represents hydrogen, $(C_1-C_6)$-alkyl, $(C_3-C_6)$-cycloalkyl, $(C_2-C_6)$-alkenyl, $(C_5-C_6)$-cycloalkenyl, phenyl, or 3- to 6-membered heterocyclyl having up to 3 hetero atoms selected from the group consisting of nitrogen, oxygen, and sulphur, where the radicals R¹ other than hydrogen are optionally substituted by one or more identical or different substituents selected from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl, and phenyl and the cyclic radicals are optionally also substituted by $(C_1-C_4)$-alkyl or $(C_1-C_4)$-haloalkyl;

R² represents hydrogen, $(C_1-C_6)$-alkyl, $(C_2-C_6)$-alkenyl, $(C_2-C_6)$-alkynyl, where the radicals R² other than hydrogen are optionally substituted by one or more identical or different substituents selected from the group consisting of halogen, hydroxyl, $(C_1-C_4)$-alkyl, $(C_1-C_4)$-alkoxy, and $(C_1-C_4)$-alkylthio;

R³ represents halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl, or $(C_1-C_4)$-alkylcarbonyl;

R⁴ represents hydrogen or methyl;

R⁵ represents halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl, or $(C_1-C_4)$-alkylcarbonyl;

n represents 0, 1, or 2, and m represents 1 or 2, or salts thereof, and 2-methoxy-N-[4-(methoxybenzoylsulphamoyl)phenyl]acetamide and other N-acylsulphonamide derivatives of formula (III)

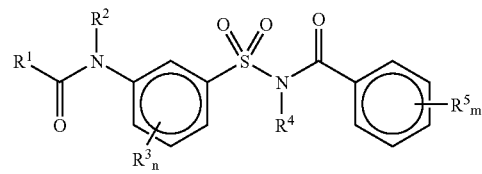

in which

R¹ represents hydrogen, $(C_1-C_6)$-alkyl, $(C_3-C_6)$-cycloalkyl, furanyl, or thienyl, where each of the radicals R¹ other than hydrogen is unsubstituted or substituted by one or more substituents selected from the group consisting of halogen, $(C_1-C_4)$-alkoxy, halo-$(C_1-C_6)$-alkoxy, and $(C_1-C_4)$-alkylthio and the cyclic radicals are optionally also substituted by $(C_1-C_4)$-alkyl and $(C_1-C_4)$-haloalkyl;

$R^2$ represents hydrogen or methyl;

$R^3$ represents halogen, halo-$(C_1-C_4)$-alkyl, halo-$(C_1-C_4)$-alkoxy, $(C_1-C_4)$-alkyl, $(C_1-C_4)$-alkoxy, $(C_1-C_4)$-alkylsulphonyl, $(C_1-C_4)$-alkoxycarbonyl, or $(C_1-C_4)$-alkylcarbonyl;

$R^4$ represents hydrogen or methyl;

$R^5$ represents halogen, $(C_1-C_4)$-alkyl, halo-$(C_1-C_4)$-alkyl, halo-$(C_1-C_4)$-alkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl, or $(C_1-C_4)$-alkylcarbonyl;

n represents 0, 1, or 2, and m represents 1 or 2, or alkali metal salts thereof.

2. A composition according to claim 1 wherein component (b) is profoxydim, bispyribac-sodium and/or pyribenzoxim.

3. A composition according to claim 1 wherein component (b) is bispyribac-sodium.

4. A composition according to claim 1 wherein component (b) is pyribenzoxim.

5. A composition according to claim 1 wherein from 0.01 to 1,000 parts by weight of the active compound of component (b) are present per part by weight of the active compound of formula (I).

6. A composition according to claim 1 wherein from 0.001 to 1,000 parts by weight of component (c) are present per part by weight of the active compound of formula (I) or mixtures of the active compound of formula (I) with active compounds of component (b).

7. A method for controlling unwanted vegetation comprising allowing an effective amount of a composition according to claim 1 to act on plants and/or their habitat.

8. A process for preparing a composition according to claim 1 comprising mixing active compounds of components (a) and (b) and, optionally, component (c) with one or more extenders and/or surfactants.

9. A composition according to claim 1 wherein component (b) is profoxydim.

* * * * *